(12) United States Patent
Alsharaeh et al.

(10) Patent No.: US 10,149,862 B2
(45) Date of Patent: Dec. 11, 2018

(54) METHOD OF MAKING NANOCOMPOSITES OF METAL OXIDE AND REDUCED GRAPHENE OXIDE AND USE FOR CANCER TREATMENT

(71) Applicants: Edreese H Alsharaeh, Riyadh (SA); Faheem Ahmed, Riyadh (SA); Nishat Arshi, Riyadh (SA); Yasmin Mussa, Riyadh (SA); Meshael Alturki, Riyadh (SA); Yazeed Aldawsari, Riyadh (SA); Azmat Khan, Riyadh (SA)

(72) Inventors: Edreese H Alsharaeh, Riyadh (SA); Faheem Ahmed, Riyadh (SA); Nishat Arshi, Riyadh (SA); Yasmin Mussa, Riyadh (SA); Meshael Alturki, Riyadh (SA); Yazeed Aldawsari, Riyadh (SA); Azmat Khan, Riyadh (SA)

(73) Assignee: Alfaisal University, Riyadh (SA)

( * ) Notice: Subject to any disclaimer, the term of this patent is extended or adjusted under 35 U.S.C. 154(b) by 115 days.

(21) Appl. No.: 14/943,213

(22) Filed: Nov. 17, 2015

(65) Prior Publication Data

US 2017/0136062 A1    May 18, 2017

(51) Int. Cl.
  *A61K 41/00* (2006.01)
  *A61K 33/26* (2006.01)
  *A61K 31/704* (2006.01)
  *B82Y 40/00* (2011.01)
  *B82Y 30/00* (2011.01)

(52) U.S. Cl.
  CPC .......... *A61K 33/26* (2013.01); *A61K 31/704* (2013.01); *B82Y 30/00* (2013.01); *B82Y 40/00* (2013.01)

(58) Field of Classification Search
  CPC .. A61K 47/48861; A61K 33/44; A61K 33/24; A61K 33/26; B82Y 5/00; B82Y 15/00; C01B 32/192; C01B 32/182
  USPC ................... 977/904, 915
  See application file for complete search history.

(56) References Cited

U.S. PATENT DOCUMENTS

| | | | |
|---|---|---|---|
| 2016/0099466 A1* | 4/2016 | Kim ....................... | H01M 4/366 252/507 |
| 2016/0204416 A1* | 7/2016 | Wu ......................... | H01M 4/131 429/218.1 |
| 2017/0143762 A1* | 5/2017 | Molokanova .......... | A61K 33/44 |

FOREIGN PATENT DOCUMENTS

| | | | | |
|---|---|---|---|---|
| CN | 102903531 A | * | 1/2013 | ............. H01G 9/042 |
| KR | 101347139 B1 | * | 1/2014 | ............. H01M 4/366 |

OTHER PUBLICATIONS

Khan ("Graphene based metal and metal oxide nanocomposites: synthesis, properties and their applications." J. Mater. Chem. A, 3, 18753-18808) (Year: 2015).*
Ma ("A Functionalized Graphene Oxide-Iron Oxide Nanocomposite for Magnetically Targeted Drug Delivery, Photothermal Therapy, and Magnetic Resonance Imaging." Nano Res. 2012, 5(3): 199-212).*
Zhu ("Microwave assisted synthesis of a-Fe2O3/reduced graphene oxide as anode material for high performance lithium ion batteries." NewJ.Chem., 2015, 39, 7923).*
Zheng ("Restoring Basal Planes of Graphene Oxides for Highly Efficient Loading and Delivery of (β-Lapachone" Mol. Pharmaceutics 2012, 9, 615-621).*
Fan ("Magnetic Fe3O4—graphene composites as targeted drug nanocarriers for pH-activated release." Nanoscale, 2013, 5, 1143).*
Kong ("Interconnected 1D Co3O4 nanowires on reduced graphene oxide for enzymeless H2O2 detection." Nano Research, 8(2): 469-480, Feb. 2015. (Year: 2015).*
Ren "Ultrasensitive dual amplification sandwich immunosensor for breast cancer susceptibility gene based on sheet materials." Analyst, 2014, 139, 3061. (Year: 2014).*

* cited by examiner

*Primary Examiner* — Tri V Nguyen
(74) *Attorney, Agent, or Firm* — Geeta Kadambi; Riddhi IP LLC

(57) ABSTRACT

A facile approach is described to prepare monodisperse $Fe_3O_4$ and $Co_3O_4$ nanoparticles on chemically reduced graphene oxide (rGO) to form nanocomposites by low temperature solution route and MWI method, respectively. These processes are environmentally friendly and convenient compared with previously reported methods. The synthesized nanocomposites were characterized using x-ray diffraction spectroscopy (XRD), raman spectroscopy, scanning electron microscopy (SEM) measurements and UV/Vis absorption spectroscopy. XRD patterns revealed the high crystalline quality of the nanocomposites. SEM micrographs showed the morphology of the rGO nanosheets decorated by $Co_3O_4$ and $Fe_3O_4$ nanoparticles. UV/Vis study revealed the formation of $Fe_3O_4$/rGO and $Co_3O_4$/rGO nanocomposites with characteristics absorption maxima. Finally, preliminary results of using the $Fe_3O_4$/rGO and $Co_3O_4$/rGO composites for efficient killing of Human hepatocytes cancer ($HepG_2$) cell are reported. Nanocomposites produced by MWI showed better anticancer activity and higher yield than that of low temperature solution route.

10 Claims, 5 Drawing Sheets

METHOD OF MAKING NANOCOMPOSITES OF METAL OXIDE AND REDUCED GRAPHENE OXIDE AND USE FOR CANCER TREATMENT

FIELD OF TECHNOLOGY

The present disclosure relates to a novel composition of metal oxide and reduced graphene oxide nanocomposite, used for treating cancer. More specifically method of making metal oxide and reduced graphene nanocomposite and a method of using the same to reduce the number of cancer cells are described.

BACKGROUND

Graphene, as a single-layer of graphitized carbon atoms, is known as a rising star among the most famous nanostructures, because its unique and fascinating properties have been highly excited fundamental researches as well as promising nanotechnology-based applications. Recently, graphene based nanomaterials have been highly induced promising advances in, e.g., biology and medicine including cancer cell targeting, imaging, and therapy, drug delivery, antiviral, bactericidal as well as nematocidal nanomaterials, tissue engineering, and neural cell and network regeneration.

Recently, the development of drug delivery system using different inorganic nanomaterials, such as Au nanoparticles, magnetic nanomaterials, and carbon nanotubes has been exploited widely. Among various inorganic nanoparticles, magnetic nanoparticles (e.g., $Fe_3O_4$, $Fe_2O_3$, $Co_3O_4$ and FePt) have their own advantages that provide many exciting and unique features in biomedical applications. For example, magnetic nanoparticles can be manipulated by an external magnetic force, so we can do the magnetically guided drug delivery using magnetic nanoparticles. Moreover, magnetic nanoparticles play an important role as magnetic resonance imaging (MRI) contrast agents because of their superparamagnetic and biocompatible properties. Therefore, magnetic nanoparticle-based drug carriers combine the functions of diagnosis and therapeutics, which is referred to as theranostics, have attracted more and more attentions.

There is a need to find an optimal method to create a nanocomposite that has superior physical and chemical properties and is easy to make.

SUMMARY

The present disclosure describes a metal oxide with reduced graphene oxide nanocomposite composition and its use as an anti-cancer nanocomposite. In one embodiment, a metal oxide is used with graphene oxide to form a nanocomposite. In another embodiment, the nanocomposite is used for treating cancer by reducing the viable cells in-vitro. In another embodiment, the metal oxides are iron oxide and cobalt oxide.

In one embodiment, the nanocomposite comprises of reduced graphene oxide, iron oxide ($Fe_3O_4$) and cobalt oxide ($Co_3O_4$). In one embodiment, the nanocomposite is made using microwave. In another embodiment, a reduced graphene oxide is combined with iron oxide and cobalt oxide individually. The cobalt oxide mixed nanocomposite was made using microwave method and the iron oxide was made using low temperature method (80° C.). Treating cancer cells, in one embodiment, using iron oxide nanocomposite to reduce number of live cells in-vitro.

In one embodiment, a combination of cobalt oxide and reduced graphene oxide to make a nanocomposite to reduce cancer cell growth in-vitro. The nanocomposite, in one embodiment, is made by using microwave irradiation (MWI). In one embodiment, no solvent was used to make the nanocomposite.

The method of making the nanocomposite and using the nanocomposite disclosed herein may be implemented in any means for achieving various aspects, and may be executed to be used for various therapeutic applications. Other features will be apparent from the accompanying drawings and from the detailed description that follows.

BRIEF DESCRIPTION OF FIGURES

Example embodiments are illustrated by way of example and no limitation in the accompanying figures and tables, like references indicate similar elements and in which.

Figure 1A:
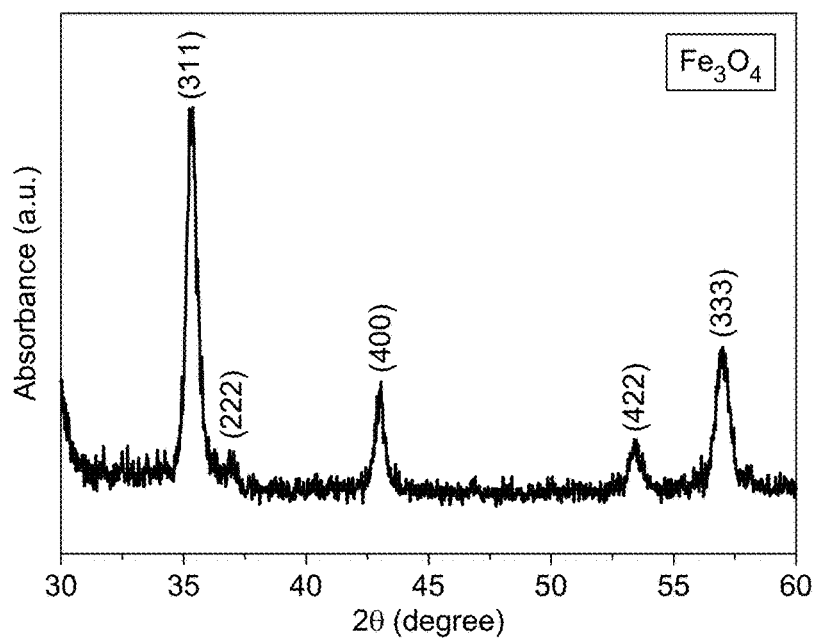
FIG. 1A shows XRD patterns of $Fe_3O_4$ nanoparticles and 1B shows XRD patterns of $Fe_3O_4$/rGO nanocomposites prepared at 80 ° C.

Other features of the present embodiments will be apparent from the accompanying drawings and from the detailed description that follows.

DETAILED DESCRIPTION

In the instant invention the preparation of the nanocomposite using low temperature and microwave method, characterization and evaluation of the Structural, morphological, and optical properties is described. More specifically method of making the nanocomposite using metal oxide and oxidized graphene oxide using a microwave method and low temperature solution method is described. The resultant metal oxide/graphene oxide nanocomposite is used to reduce the cell count of cancer cells in-vitro. The nanocomposite may form a part of an ongoing cancer therapy treatment, used in-vivo or used for testing cancer reducing properties along with other pharmaceutical products or by themselves.

Nowadays, novel grapheme oxide (GO) and reduced graphene oxide (rGO)-based nanocomposites using magnetic nanoparticles have been given much attention in a variety of biomedical applications, including drug delivery, gene delivery, and imaging. Graphene oxide moiety in the hybrids possesses large specific surface area, monoatomic layer plane structure and abundant hydroxyl, carboxyl or epoxy groups. These excellent characteristics allow it to have not only strong p-p interactions with the aromatic rings existing in many drug molecules but also capability to conjugate drug molecules by forming new chemical bond or electrostatic attraction.

Formation of $Fe_3O_4$/rGO and $Co_3O_4$/rGO nanocomposites is usually achieved by in situ reduction of iron salt and cobalt salt precursors or assembly of the magnetic nanoparticles on the GO surface. There are, however, some problems with the approaches reported so far, such as poor control over the size, size distribution, and location of magnetic nanoparticles on the GO sheets. All these drawbacks make the use of magnetic nanoparticles/rGO nanocomposites in biomedical and other fields difficult.

In this work, $Co_3O_4$/rGO and $Fe_3O_4$/rGO were synthesized using MWI and low temperature solution route, respectively. Cytotoxicity of these nanocomposites on human liver cells ($HepG_2$ cell line) was studied. Nanocomposites prepared by MWI showed higher yield of the product as well as better anticancer activity than that of low temperature route.

Experimental Details

All the chemicals used in this investigation were AR-grade materials and used without further purification. Cobalt Acetate(II) Tetrahydrate (($CH_3COO)_2Co.4H_2O$ 95%), Ferric nitrate (Fe $(NO_3)_3 \cdot 9H_2O$), polyethyleneglycol (PEG), ferric chloride, ferric sulfate, and hydrazine hydrate ($N_2H_2OH$ 80%) were purchased from Loba Chemie. However, cetyl trimethyl ammonium bromide (CTAB 98.0%) was purchased from central drug house. Ethanol absolute ($C_2H_5OH$ 99%) was purchased from Scharlau. De-ioinized water was used to prepare aqueous solutions.

Synthesis of $Co_3O_4$ nanoparticles and $Co_3O_4$/rGO nanocomposites : 920 mg of CTAB was mixed with 800 ml of distilled water and 8% (2 mg/ml) graphene oxide (synthesized by the hummer's method) in a 1000 ml beaker. After 30 minutes of continuous stifling, a mixture of 4.6 g of cobalt acetate in 333 ml distilled water was added drop wise to the solution. Next, 1 ml of the reducing agent hydrazine hydrate was added to the solution. The solution was heated under microwave irradiation for 20 minutes with a power of 100 W; then the product was washed several times by distilled water and ethanol and then was dried at 80° C. overnight. The dried sample was ground and calcined at 600 ° C. for 2 h. A black coloured product was obtained. In addition, pure $Co_3O_4$ nanoparticles and RGO were synthesized by the same method.

Synthesis of $Fe_3O_4$ nanoparticles and $Fe_3O_4$/rGO nanocomposites: In this sample 2 g ferric chloride and 2 g ferric sulfate were mixed with 0.4 g (8%) graphene oxide (synthesized by the hummer's method) in 50 ml deionized water and stirred to maintain a homogenous solution. Then, 8 ml of 25% ammonia solution was added drop wise under vigorous stifling in which 8 ml PEG was also added quickly before heating the solution to 80 ° C. on a hot plate. After that, the solution was washed by centrifugation at 3000 rpm several times with deionized water and with ethyl alcohol diluted to 70%) followed by drying the sample at 80° C. in the oven overnight.

Anticancer Activity

Cells and Reagents. Human cancer cell lines HepG2 (Liver) were grown in RPMI media supplemented with 10% bovine serum, 1X penicillin-streptomycin (HyClone Laboratories) at 37° C. in a humified chamber with 5% $CO_2$. Doxorubicin (sigma) was used as the reference drug (standard).

Treatment. Cells were seeded ($10^5$ cells/well in triplicate) in a 96-well flat-bottom plate (Becton-Dickinson Labware) a day before treatment and grown. Stocks of all extracts/compound (1.0 mg/ml) were made with 10% DMSO (Sigma) and further working solutions (100 µg/ml) were prepared in serum-free culture media. Cells were treated with four different doses (25, 50, 100 and 200 µg/ml; in triplicate) of the compounds, in complete growth media, including reference drug, and further incubated for 48 hours.

Cell Proliferation and Viability Assay. On day 2 of treatment, cell proliferation and viability test was performed using TACS MTT Cell Proliferation and Viability Assay Kit (TACS) as per manufacturer's instructions. The relationship between surviving fraction and compound concentration was plotted to obtain the survival curve of cancer cell lines. The response parameter calculated was the $IC_{50}$ value, which corresponds to the concentration required for 50% inhibition of cell viability.

Results and Discussion

Figure 1B:
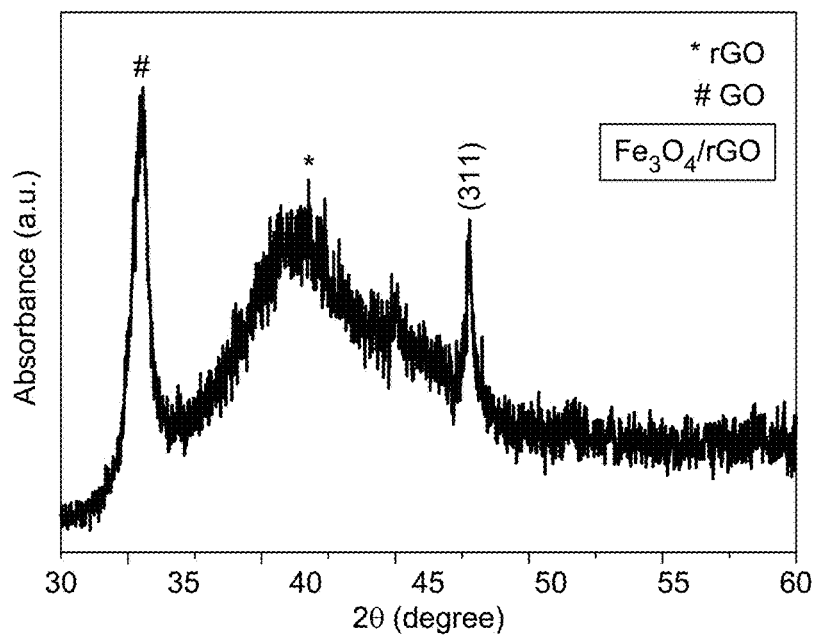

XRD patterns were used to investigate the phase and structure of $Fe_3O_4$, $Co_3O_4$, rGO, $Fe_3O4$/rGO, and $Co_3O4$/rGO nanocomposites. XRD patterns of $Fe_3O4$ and $Fe_3O4$/rGO nanocomposites are presented in FIG. 1 and $Fe_3O4$/rGO composites displayed different XRD patterns from $Fe_3O4$. In the XRD pattern of $Fe_3O4$, all the peaks can be assigned to the cubic $Fe_3O4$ which is well matched with the JCPDS card No. 86-1359. While, in the XRD pattern of $Fe_3O4$/rGO, the characteristic peak (002) of graphite at 26.5° disappeared after oxidation, while an additional peak at 11.22° was observed, which was corresponding to the (001) diffraction peak of GO. Not only that, but the d-spacing of GO was larger than that of graphite. The larger interlayer distance of GO might be due to the formation of oxygen-containing functional groups, such as hydroxyl, epoxy and carboxyl. Thus, from the XRD pattern of $Fe_3O_4$/rGO, it could be inferred that the original graphite powders had almost been completely oxidized. A broad diffraction peak (002) of rGO at about 24.1° was observed in the XRD pattern of $Fe_3O4$/rGO composites. The broadening and shift of the characteristic diffraction peak of graphite from 26.5° to 24.1° was due to the short-range order in stacked stacks. The interlayer spacing of rGO is slightly larger than that of graphite, which was resulted from the small amount of residual oxygen-containing functional groups or other structural defects.

Figure 2:
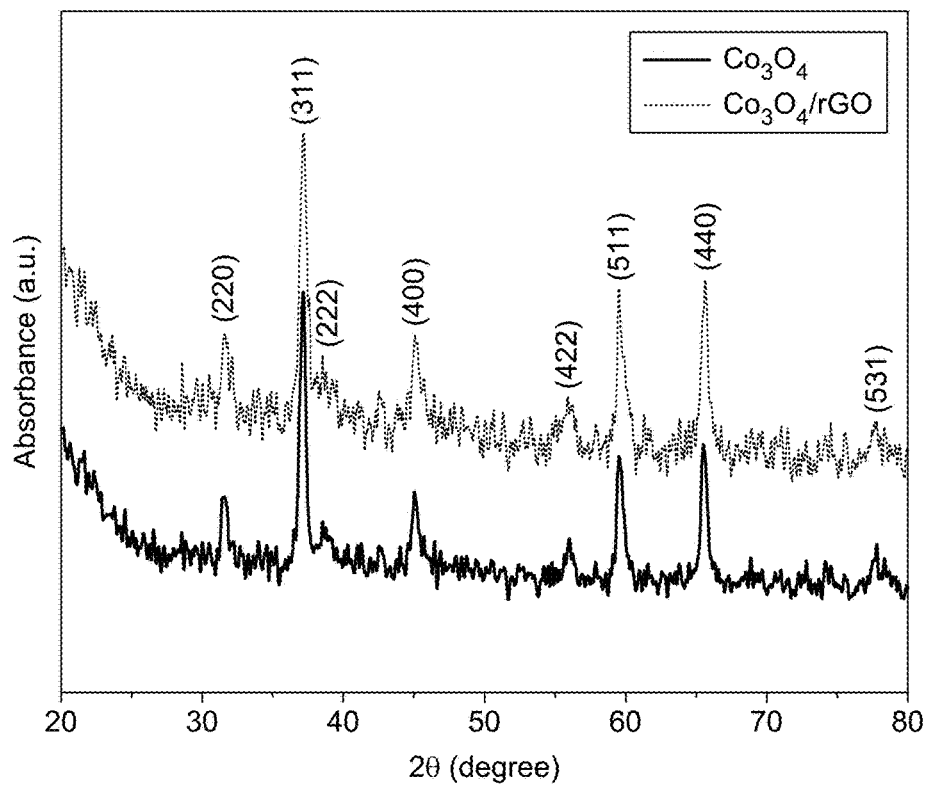
FIG. 2 shows XRD patterns of $Co_3O_4$ nanoparticles and $Co_3O_4$/rGO nanocomposites prepared by MWI.

FIG. 2 shows the XRD patterns of $Co_3O4$ and $Co_3O_4$/rGO nanocomposites. The positions and relative intensities of the diffraction peaks matched well with the standard XRD data of spinal $Co_3O_4$ (JCPDS card No. 71-0816), while the characteristic diffraction peak of graphite located at 26.4° couldn't be observed, revealing that $Co_3O_4$ nanoparticles were efficiently deposited on the graphene surface, suppressing the stacking of graphene layers, and no graphite-like layered structure was formed by re-stacking of chemically reduced graphene in this condition. Therefore, the diffraction peak of graphite disappeared in the XRD patterns of the $Co_3O_4$/rGO nanocomposites. XRD observation confirmed the effective reduction of GO and the successful deposition of $Co_3O_4$ nanoparticles on the surfaces of rGO sheets by the MWI reaction.

Figure 3:
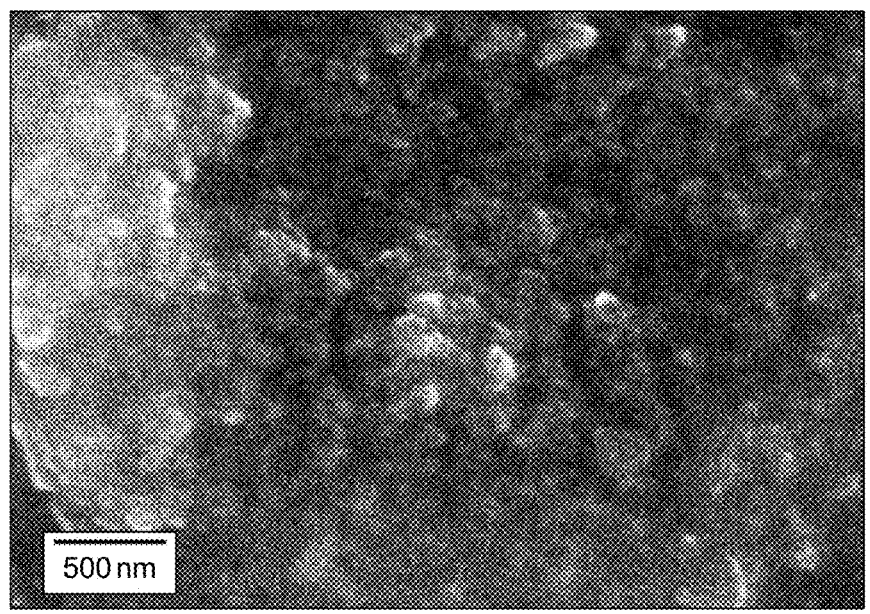
FIG. 3 shows SEM image of $Fe_3O_4$ nanoparticles.
Figure 4B:
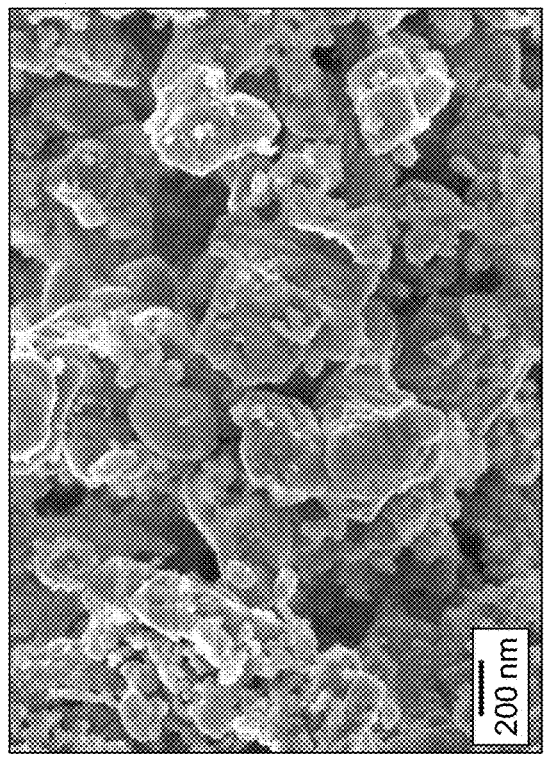
FIG. 4A shows SEM images of $Co_3O_4$ nanoparticles, and 4B shows SEM images of $Co_3O_4$/rGO nanocomposites prepared by MWI.
Figure 4A:
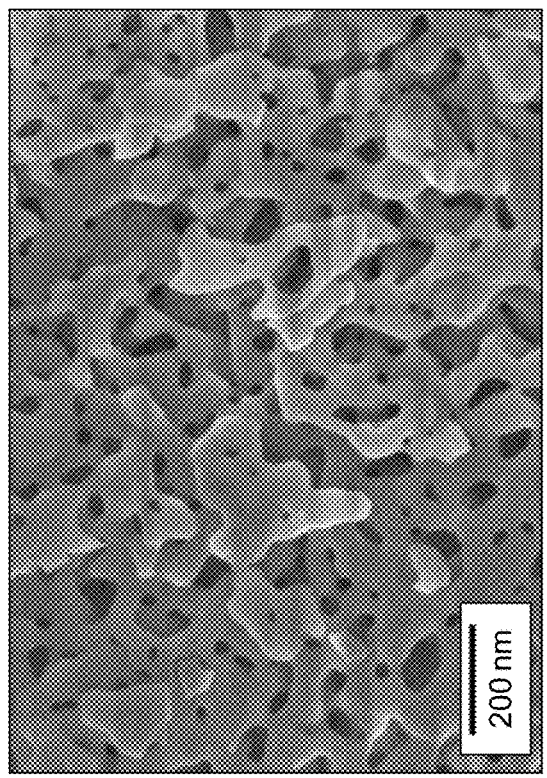

FIG. 3 shows SEM images of the $Fe_3O_4$ nanoparticles. The SEM images of the $Co_3O_4$ NPS and $Co_3O_4$/rGO composite are presented in FIG. 4. FIG. 4(*a*) shows the SEM images of pure $Co_3O_4$ nanoparticles in which nanoporous structure is seen. As one can see from FIG. 4*b*, ~20 nm sized $Co_3O_4$ nanoparticles uniformly dispersed on the surface of rGO sheets, and effectively prevented the aggregation of $Co_3O_4$ nanoparticles and graphene restacking. Moreover, it clearly demonstrated that a relatively larger amount of $Co_3O_4$ nanoparticles deposited on the surface of rGO. All these results indicate the successful preparation of $Fe_3O_4$/rGO and $Co_3O_4$/rGO nanocomposites.

Figure 5A:
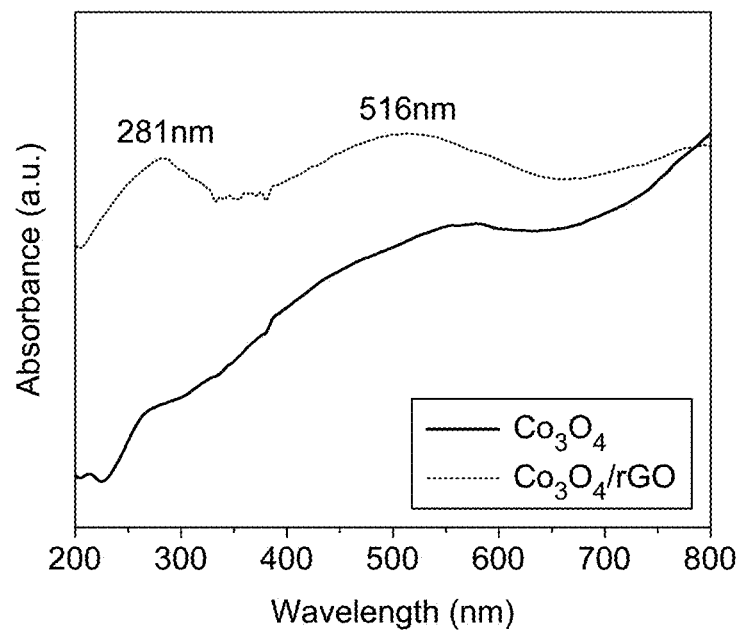
FIG. 5A shows UV-Vis absorption spectra of $Co_3O_4$/rGO nanocomposites and 5B shows UV-Vis absorption spectra of $Fe_3O_4$/rGO nanocomposites.
Figure 5B:
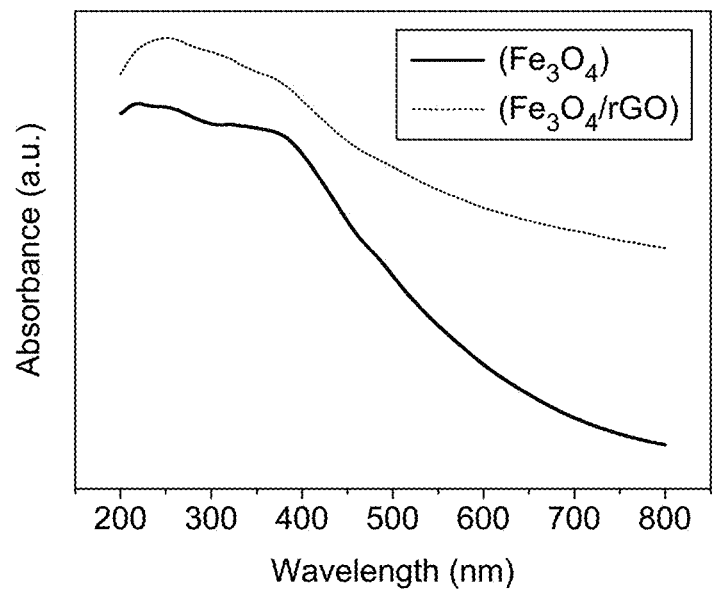

Optical properties of the as prepared $Co_3O_4$ nanoparticles, $Fe_3O4$ nanoparticles, $Fe_3O_4$/rGO and $Co_3O_4$/rGO nanocomposites were investigated by UV-Vis spectroscopy. FIG. 5 (a) shows that the absorbance spectrum of the as-prepared $Co_3O_4$ has two absorbance bands in 200 to 350 nm and 400 to 580 nm wavelength range. The first band is because of the $O^{2-} \rightarrow Co^{2+}$ charge transfer process and the second band is because of the $O^{2-} \rightarrow Co^{3+}$ charge transfer process. In case of $Fe_3O_4$ nanoparticles, clear absorption band around 410 nm is observed. In addition, the absorbance spectrum of the $Co_3O_4$/rGO nanocomposites (FIG. 5(a)) and $Fe_3O_4$/rGO nanocomposites (FIG. 5(b)) shows and absorbance band at 230 nm for $Fe_3O_4$/rGO and 281 nm for $Co_3O_4$/rGO, which is attributed to characteristic absorption band of rGO.

Figure 6:
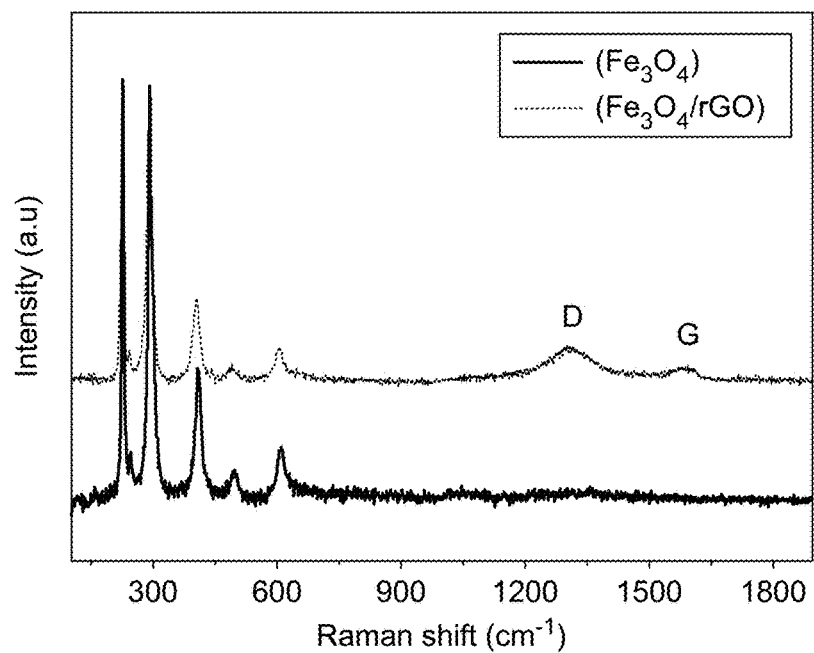
FIG. 6. Raman spectra of $Fe_3O_4$ nanoparticles and $Fe_3O_4$/rGO nanocomposites.
Figure 7:
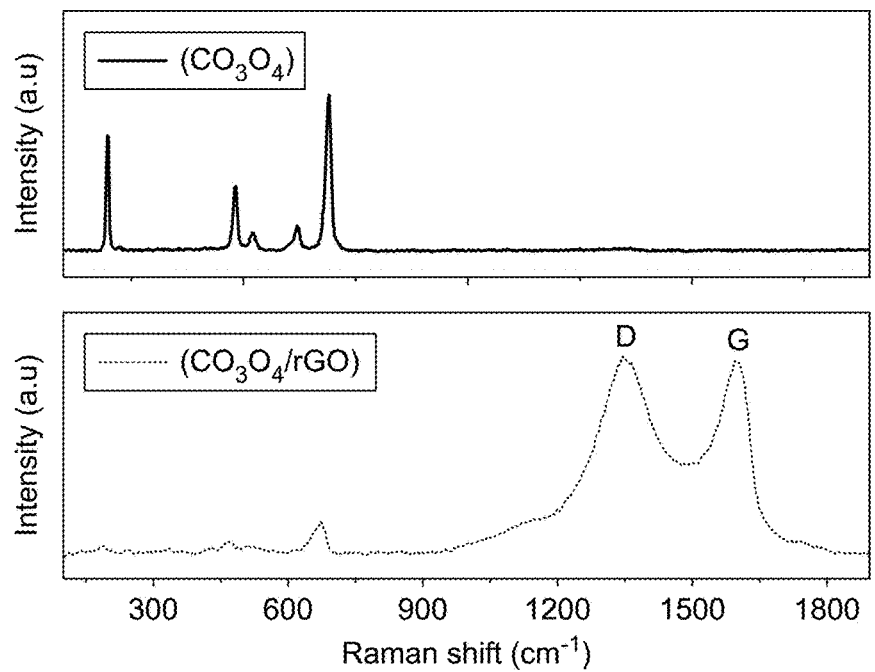
FIG. 7. Raman spectra of $Co_3O_4$ nanoparticles and $Co_3O_4$/rGO nanocomposites.

FIG. 6 shows the Raman spectra of $Fe_3O_4$ nanoparticles and Fe3O4/rGO nanocomposites. It is clear that the Raman bands at 220.2 and 491.2 $cm^{-1}$ could be assigned to the scattering of A1g mode of Fe3O4, while the bands at 284, 398 and 601 $cm^{-1}$ were attributed to the scattering of $E_g$ mode of Fe3O4. The Raman spectra of the composites had several typical peaks of the Fe-O stretching vibration, indicating that Fe3O4/rGO composites were successfully synthesized. Besides, the intensity of the bands corresponding to Fe3O4 decreased in the composites. The characteristic D and G bands for the composites were observed at 1322 and 1594 $cm^{-1}$, respectively. FIG. 7 shows the Raman spectra of the $Co_3O_4$ nanoparticles and Co3O4/rGO nanocomposites. The peaks at 1348 $cm^{-1}$ and 1599 $cm^{-1}$ were attributed to sp3 (D band) and sp2 (G band) hybridization carbon atoms, respectively. Peaks at 194, 476, 522 and 681 $cm^{-1}$ were ascribed to the $F_{2g}$, Eg, $F_{2g}$ and $A_1g$ modes in Co3O4, respectively.

It is well known that the D band is associated with the disordered samples or graphene edges, while the G band is the result of the first-order scattering of the $E_{2g}$ mode of sp2 carbon domains. Both the position and intensity of D and G bands are highly susceptible to the structural changes of the carbon matrix, and there are many factors which can affect the position and intensity of D and G bands, such as doping, layer numbers, defects, strains, substrates, etc.

All the synthesized nanoparticles and nanocomposites were evaluated against a human cancer cell lines $HepG_2$ (Liver), and the results are collected in Table 1. Cells were treated with the test compounds at concentrations ranging from 25, 50, 100 and 200 µg/ml; in triplicate, for 48 h. The results are expressed in $IC_{50}$ values of the indicated compounds tested against the different cell lines and doxorubicin was used as a reference drug. Both the nanocomposites possess an anti-proliferative activity against HepG2 (Liver) cell lines, and $Co_3O_4$/rGO nanocomposites is particularly efficient in inhibiting cell proliferation (Table 1) and found to be more potent than the standard which could be due to the presence of aminoquinoline and amino methylthiazole group. Moreover, $Fe_3O_4$/rGO showed moderate cytotoxicity against HepG2 cancer cell lines suggesting that the presence of 2-amino-4-methylthiazole group was beneficial, while pure $Fe_3O_4$, $Co_3O_4$, and rGO showed very less sensitivity.

TABLE 1

$IC_{50}$ values of the prepared nanoparticles and nanocomposites for HepG2 cancer cell line:

| Sample | $IC_{50}$ (µg/ml) |
| --- | --- |
| $Fe_3O_4$ | 200 |
| $Fe_3O_4$/rGO | 100 |
| $Co_3O_4$ | 100 |
| $Co_3O_4$/rGO | 50 |

In summary, we have developed a simple, cheap and cost effective process to synthesize $Co_3O_4$/rGO nanocomposites by MWI and $Fe_3O_4$/rGO nanocomposites by low temperature solution route. The nanoparticles with an average size of 10-30 nm are uniformly anchored on rGO sheets. The nanocomposite prepared by MWI shows remarkable anti-cancer activity for HepG2 cancer cell line compared to the nanocompsoites prepared by low temperature route. This improved performance could be attributed to the formation of 2D rGO framework decorated with well-dispersed $Co_3O_4$ nanoparticles. This structural feature of the rGO-based magnetic composites facilitates efficient loading of anticancer drugs onto the basal region of the rGO sheets. This approach may be generalized to form a wide variety of NP-rGO composites, by simply changing the type of nanoparticles and the ratio of NPs to rGO, adaptable to different applications.

In addition, it will be appreciated that the various compositions and method of making the nanocomposite disclosed herein may be embodied using means for achieving the various combinations of nanocomposite using microwave irradiation doses. Accordingly, the specification and drawings are to be regarded in an illustrative rather than a restrictive sense.

What is claimed is:

1. A method to make a $Co_3O_4$/reduced graphene oxide (rGO) nanocomposite to treat a human cancer cell line, comprising:
   stirring a solution of cetyl trimethyl ammonium bromide and a graphene oxide solution for 30 minutes;
   mixing a cobalt acetate solution in water to a stirred solution dropwise to make a solution;
   adding a reducing agent to the solution;
   irradiating the solution after adding the reducing agent in a microwave using a specific power to make a product;
   washing the product several times using a water and an ethanol;
   drying a washed product at 80° C. for two hours;
   calcining and grinding a dried product to obtain the $Co_3O_4$/rGO nanocomposite;
   adding the $Co_3O_4$/rGO nanocomposite at various concentrations to a human cancer cell line; and
   inhibiting the cell proliferation of the human cancer cell line.

2. The method of claim 1, further comprising;
   adding the $Co_3O_4$/rGO nanocomposite at a concentration between 25-200ug/ml of a cell media.

3. The method of claim 1, wherein the specific power of the microwave is 100W.

4. The method of claim 1, wherein the graphene oxide solution has a concentration of 2mg/ml.

5. The method of claim 1, wherein the reducing agent is hydrazine hydrate.

6. A method of making a black colored metal oxide/ reduced graphene oxide nanocomposite to treat a human cancer cell line, comprising:
   adding a cationic surfactant dissolved in a distilled water to a graphene oxide solution to make a homogeneous solution;
   stirring the homogeneous solution and adding a second compound solution dropwise to make a solution, wherein the second compound solution is cobalt acetate solution;
   stirring the solution and adding a reducing agent to make a processed solution;
   microwaving the processed solution at a specific power for 20 minutes to obtain a $Co_3O_4$/reduced graphene oxide (rGO) nanocomposite; and washing the $Co_3O_4$/reduced graphene oxide nanocomposite with water and ethanol and drying at 80° C. overnight to obtain a dried sample;

grinding the dried sample and calcining at 600° C. for 2 hours to obtain the black colored $Co_3O_4$/reduced graphene oxide nanocomposite;

adding the black colored $Co_3O_4$/rGO nanocomposite at various concentrations to the human cancer cell line and inhibiting the cell proliferation of the human cancer cell line.

7. The method of claim 6, wherein the reducing agent is hydrazine hydrate.

8. The method of claim 6, wherein the specific power of the microwave is 100W.

9. The method of claim 6, further comprising;

adding the $Co_3O_4$/rGO nanocomposite at a concentration between 25-200ug/ml of a cell media.

10. The method of claim 6, wherein the graphene oxide solution is made at 2mg/ml.

* * * * *